United States Patent [19]

Ranalletta et al.

[11] Patent Number: 4,905,724

[45] Date of Patent: Mar. 6, 1990

[54] METERING VALVE FOR HEPARIN OR THE LIKE

[75] Inventors: Joseph V. Ranalletta; Joseph J. Cerola, both of Guntersville, Ala.

[73] Assignee: Ryder International Corporation, Arab, Ala.

[21] Appl. No.: 283,374

[22] Filed: Dec. 12, 1988

[51] Int. Cl.[4] .............................................. F16K 31/12
[52] U.S. Cl. ...................................... 137/114; 137/499
[58] Field of Search .................... 137/114, 111, 512.4, 137/499

[56] References Cited

U.S. PATENT DOCUMENTS

| 2,745,628 | 5/1956 | Carlson | 251/83 |
| 3,141,471 | 7/1946 | Williamson | 137/114 |
| 4,022,245 | 5/1977 | Davis | 137/559 |
| 4,542,768 | 9/1985 | Harris | 137/857 X |

FOREIGN PATENT DOCUMENTS

| 520123 | 12/1955 | Canada | 137/114 |
| 708419 | 4/1965 | Canada | 137/499 |
| 815472 | 10/1951 | Fed. Rep. of Germany | 137/114 |

OTHER PUBLICATIONS

Haemonetics, "Rapid Infusion System", (11 page brochure).

Primary Examiner—Alan Cohan
Attorney, Agent, or Firm—R. A. Giangiorgi

[57] ABSTRACT

A material regulating valve which controls the flow of an additive material into a primary material as a function of the volume, flow rate, and viscosity of the primary material. The device is comprised of a two sectioned body with a primary flow path and an additive flow path through the body such that the additive flow path intersects the primary flow path at one portion in the body. Located between the primary flow path and the additive flow path is a additive flow regulating component. The device also included a flow indicator which provides a visual confirmation when material is flowing through the primary path and a manual control component which provides a manual over ride of the normally self controlling flow regulating component.

10 Claims, 2 Drawing Sheets

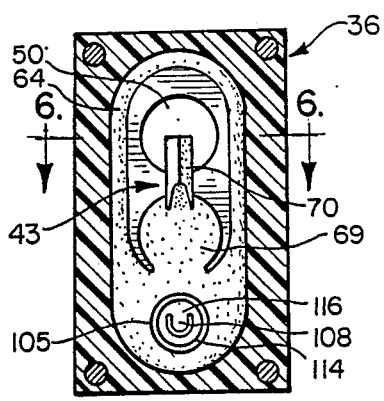
FIG. 4
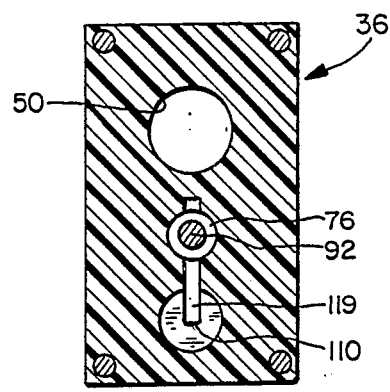
FIG. 5
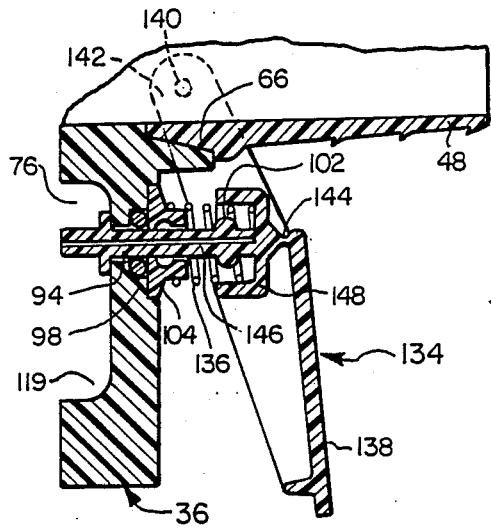
FIG. 7
FIG. 6
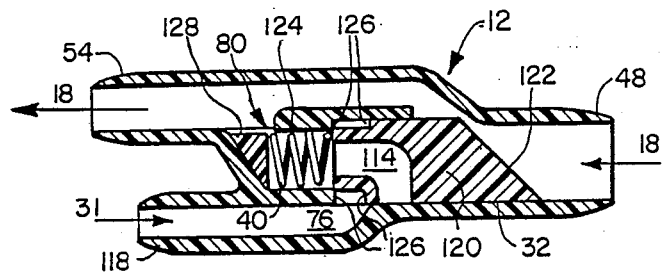
FIG. 8
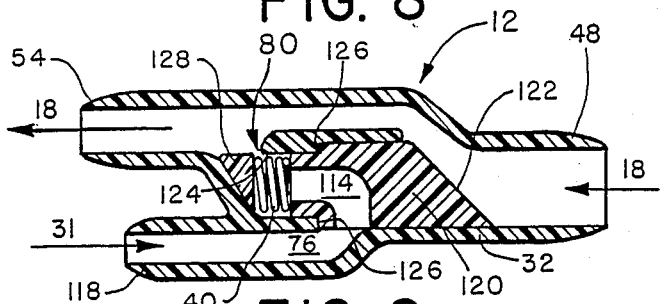
FIG. 9
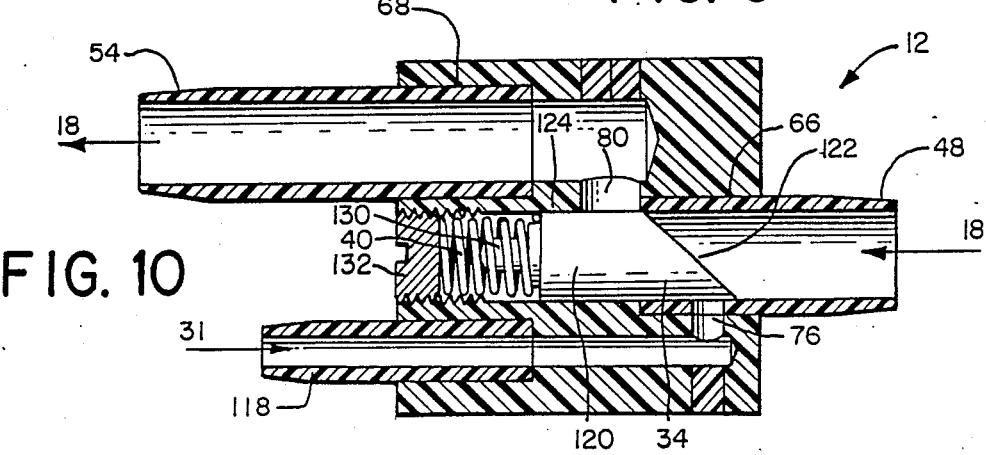
FIG. 10

METERING VALVE FOR HEPARIN OR THE LIKE

BACKGROUND SUMMARY OF THE INVENTION

This invention relates to a material flow regulating device which controls the flow of an additive material into a stream of primary material as a function of the volume, flow rate, and viscosity of the primary material. The preferred embodiment is used as a fluid regulating device in conjunction with a blood scavenging apparatus for medical operations to regulate the flow of an anticoagulent such as Heparin into the scavenged blood as a function of the volume, flow rate, and viscosity of the scavenged blood flowing through a primary fluid line.

Fluid management is a critical factor in the success of major operations such as organ transplants, major orthopedic and vascular surgery, burn operations, and other severe trauma involving high blood loss medical procedures. The lack of consistent blood flow at a sufficient rate to replace the blood lost during these medical procedures can result in complications or death due to hypovolemic or hypothermic shock. Hypovolemic shock results when there is a sudden decrease in circulating blood volume and hypothermic shock often follows the recessitation efforts to counteract the hypovolemic shock. In the attempt to quickly replenish lost blood, blood volume is replaced with lower temperature blood or other fluids resulting in a drop in the patients body core temperature, thereby inducing hypothermic shock.

Equipment is available to provide rapid infusion of replacement blood to reduce the risk of hypovolemic shock which incorporate heating systems to reduce the risk of hypothermic shock during replenishment efforts. An example of this equipment is the Haemonetics R.I.S. TM (Rapid Infusion System) manufactured by Haemonetics Surgical Products Division, Braintree, Mass. Typically, rapid infusion systems scavenge blood from an operation site by means of a vacuum device, filter the blood, and prepare the blood for infusion back into the patient. Blood which is scavenged from and reinfused into a patient has many advantages over external source blood including confirmed blood type matching and most importantly reduced risk of contracting blood diseases such as AIDS and Hepititis.

When scavenging blood, precautions must be taken to prevent the blood from coagulating. To prevent coagulation, an anti-coagulent, such as heparin is added to the scavenged blood immediately downstream from the point of intake. The addition of an anti-coagulent prevents the scavenged blood from coagulating with other materials scavenged from the operation site such as fasts, tissue, and bone fragments and permits the blood to be filtered and re-cycled.

Typically, the addition of an anti-coagulent additive is accomplished using a steady drip of the additive into the primary scavenged blood flow. However, this method has a problem of adding too much anti-coagulent into the system when the scavenged blood flows at a low rate; and not enough anti-coagulent when the scavenged blood flow is at a higher rate. The problem with too low an anti-coagulent level is that the scavenged blood coagulates before it is processed for infusion, and the problem with too high an anti-coagulent level is that the blood will not coagulate once returned to the patient. The scavenged and recycled blood cannot have too high a concentration of the anti-coagulent because the healing process which follows the operation will be impeded as it requires the natural coagulation of blood. Therefore, the prior art system for anti-coagulent introduction creates many problems.

Further, prior art systems did not provide the medical personnel in charge of monitoring anti-coagulent flow with means which positively indicate additive flow. To solve this problem a flow meter could be attached or the volume of the feed source of the additive could be manually monitored, but meters are not always available, and manual monitoring of the anti-coagulent flow is not practical in a medical trauma situation.

SUMMARY AND OBJECTS OF THE INVENTION

An object of this invention is to provide an effective material regulating device which meters out a needed quantity of an additive material into a stream of a primary material as a function of the volume, flow rate, and viscosity of the primary material.

Another object of this invention is to provide a manual control for the material regulating device to override the automatic introduction of additive material and which also permits locking of the additive regulating means in a free flow position.

Yet another object of this invention is to provide flow indicating means to provide a visual indication of material flow through a material flow path.

In accordance with the foregoing objects, the invention comprises a material flow regulator with a two section body and two material flow paths through the body whereby a regulated additive flow path intersects a primary flow path, and additive introduction is a function of the characteristics of the material flowing through the primary flow path. The material in the primary flow path displaces regulating means located in the primary flow path to release an additive into the primary flow path. The result is that when the volume, flow rate, and/or viscosity of the material flowing in the primary flow path increases the rate of introduction of the additive material into the primary flow path increases. Likewise, when the volume, flow rate, and/or viscosity of the material flowing in the primary flow path decreases the rate of introduction of the additive material into the primary flow path decreases.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawing in which like reference numerals identify like elements, and in which:

FIG. 4 is a cross-section of the preferred embodiment of the present invention taken at 4—4 in FIG. 2 illustrating the unitary design of the additive gate means;

FIG. 5 is a cross-section of the preferred embodiment of the present invention taken at 5—5 in FIG. 2;

FIG. 6 is a cross-section taken at 6—6 in FIG. 4 showing the structure of the additive gate means;

FIG. 7 is a partial cross-sectional view of a manual control device used to override normally automatic operation of the present invention and which may be used with the embodiment of FIG. 1 and 2;

FIG. 8 is a cross-sectional view of an alternative embodiment of the present invention which shows a plunger in a position which prevents introduction of an additive material into the primary flow path;

FIG. 9 is a view of the embodiment shown in FIG. 8 with the plunger in a position which permits introduction of an additive material into a primary flow path;

FIG. 10 is a cross-section of still another alternative embodiment which shows a plunger configured for "upstream" introduction of an additive material into the primary flow path;

DETAILED DESCRIPTION OF THE ILLUSTRATED EMBODIMENT

Figure 1:
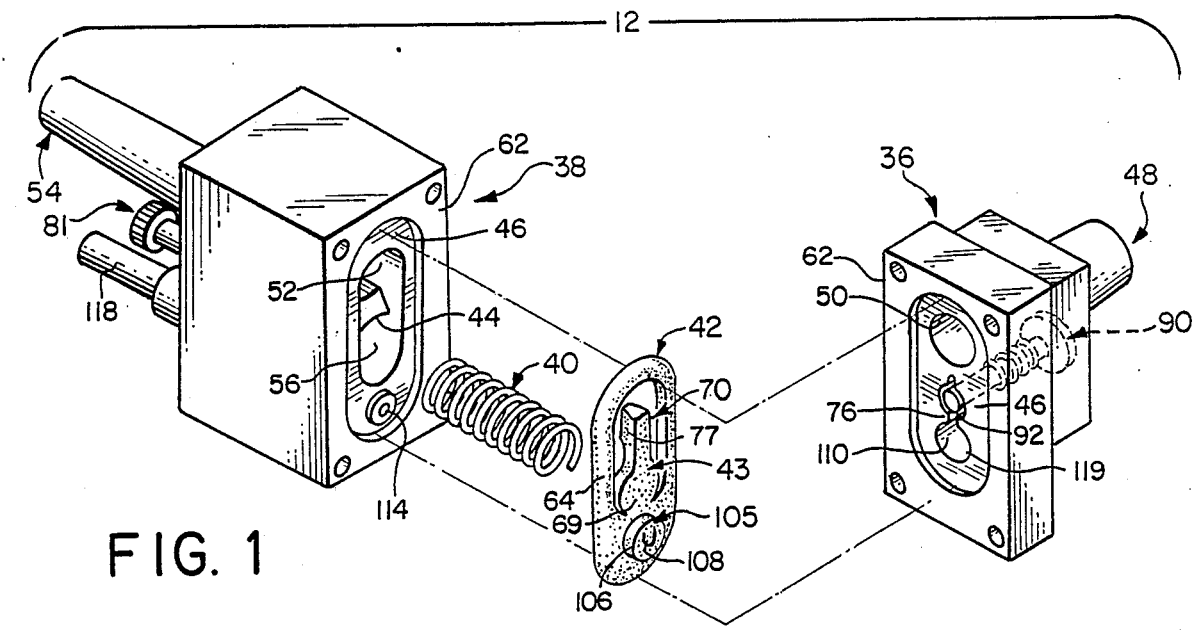
FIG. 1 is an exploded view of a preferred embodiment of the present invention.

While this invention is susceptible to embodiment in many different forms, there are shown in the drawings and will be herein described in detail preferred embodiments with the understanding that the present disclosure is to be considered an exemplification of the principals of the invention and is not intended to limit the invention to the embodiments illustrated.

Figure 3:
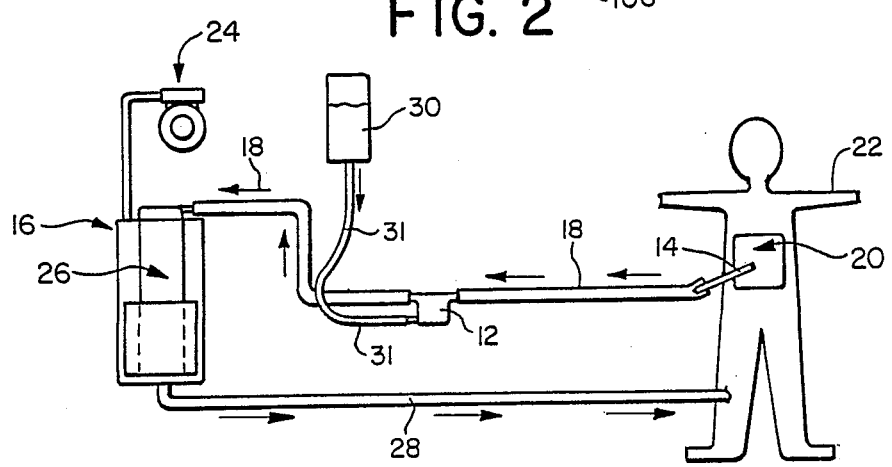
FIG. 3 is a schematic representation of a rapid infusion blood recycling system at a medical operation site in which the present invention is used.

FIG. 3 shows a schematic of the operation of a blood scavenging rapid infusion system in which the illustrated embodiment of the present invention is used. An additive metering valve device 12 is typically inserted between a collection means or tube 14 and a rapid infusion system 16 in a primary blood flow path 18. The collection means 14 collects blood at the operation site 20 of a patient 22 under a vacuum which is pulled by a vacuum pump 24 at the filtering system 16. The blood collected at the operation site 20 flows through a primary path 18 and is deposited in a reservoir 26 where it is held until it is filtered. Once filtered, the patients own blood is returned to his body through a return flow path 28 under pressure as controlled by the rapid infusion system 16.

Figure 2:
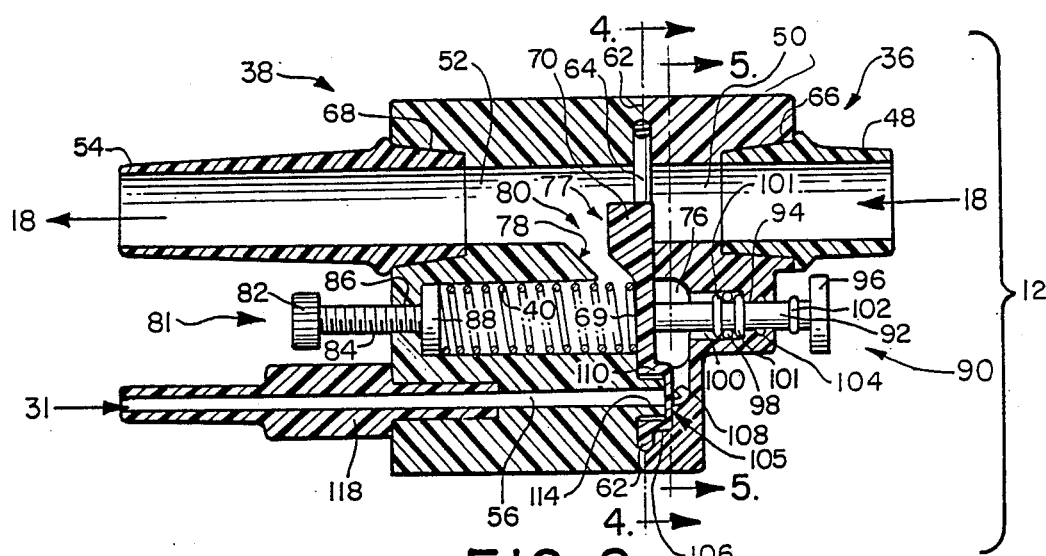
FIG. 2 is a cross-section of the preferred embodiment of the present invention illustrated in FIG. 1.

The additive metering valve 12 controllably introduces an additive, in this case an anti-coagulent additive 30, such as Heparin through an additive flow path 31, into the primary blood flow path 18. As best shown in FIGS. 2, 8, and 10 there are several embodiments which provide metering of the anti-coagulent additive 30 into the primary blood flow path 18. FIGS. 8 and 10 are based on a pass through plunger 32 and a solid plunger 34, respectively. While these two embodiments provide substantial benefits over the prior art, they will be discussed as alternatives, hereinafter, whereas the embodiment as shown in FIGS. 1 and 2 will be the focus of the initial discussion of the specification. The emphasis of the specification is not intended to limit the scope and spirit of the invention to the embodiment as shown in FIG. 1 but rather includes embodiments such as in FIGS. 8 and 10 as embracing common principles of operation as will be illustrated herein by way of description of the preferred embodiment of FIG. 7.

Turning now to FIGS. 1 through 6 to illustrate the preferred embodiment of the present invention. FIG. 1 shows an exploded view of the present invention separating a first or upstream body section 36 and downstream body sections 38 to reveal a gate or valve biasing spring 40 and additive valve or additive regulating means designated generally 42 which are mounted between the two body sections 36, 38. When assembled, the spring 40 seats in bore 44 and additive valve or regulating means 42 seats in a recessed or relieved seat feature 46 which is formed in both the upstream 36 and the downstream 38 body sections. Scavenged blood passes through the device 12 by entering through a primary flow input adapter 48, through an entry bore 50, to an exit bore 52, and out through an output adapter 54, all of which define the primary flow path 18 through the body of the device 12.

FIG. 2 is a cross section of the device 12 as shown in FIG. 1. The body of the device 12 is comprised of the upstream 36 and downstream 38 body sections (crossed hatch area on the drawing) and has three major fluid flow bores or paths: the entry bore 50, the exit bore 52, and the additive flow bore 56. The first two provide a primary flow path for the passage of blood and the third a flow path or passage for the additive. The two body sections 36,38 meet along a seam or interface 62, which generally follows section line 4—4 and is sealed by resilient annular gasket means 64 which is integrally formed as part of the flow regulating means 42. The primary flow input adapter 48 mates to the entry counter bore 66 to secure a hose leading to an operation site scavenging collection means 14, such as a suction wand, to the device 12. The output adapter 54 mates to the exit counter bore 68 to secure a hose leading to the reservoir 26.

Positioned between body sections 36, 38 is the additive regulating means 42. The regulating means 42 is formed of a resiliently deflectable material and comprises integrally formed portions including; additive gate or valve means 43, annular gasket means 64, and additive flow indicator means 105. The additive gate means 43 is further comprised of a flap-like valve portion 69 and a resiliently deflectable tongue member 70 which is integrally formed with the flap-like valve portion 69.

The resiliently deflectable tongue member (hereinafter referred to as "tongue") 70 as shown in FIG. 2 extends into the primary flow path 18 as defined by bores 50 and 52, and in operation is moved or deflected as a function of blood flow through the primary flow path 18. On the end of this tongue 70 is an integrally formed aerodynamic projection 77 which has a tear drop shaped cross-section (FIG. 10) to minimize the turbulence created by the tongue 70 projecting into the primary flow path 18. Further, the aerodynamic projection 77 controllably limits the degree of deflection of the tongue 70 by contacting the downstream wall 78 of the additive introduction channel or junction flow path 80. When the tongue 70 deflects, the valve flap 69 to which the tongue 70 is attached deflects away from the additive introduction port 76 thereby allowing additive to flow into the primary flow path 18. Under non-flow conditions, the spring 40 will bias the valve flap 69 into a "valve closed" position, wherein said valve flap 69 blocks or seals the additive introduction port 76. Thus, movement of the valve flap 69 via the tongue 70 is in response to or a function of the flow of blood in the primary flow path 18, which moves the tongue 70 downstream to unseat the flap-like valve 69. The degree to which the flap valve 69 is unseated is directly related to the character and force of the flow rate in the bores 50 and 52; which form part of the primary flow path 18.

The force of the blood flowing in the primary flow path 18 required to release the additive is adjustably controllable by using flow resistance means 81. Flow resistance means 81 is comprised of an adjustment screw 82, the threaded shaft 84 of which extends through a threaded bore 86, with a disk 88 which compresses the gate opposing spring 40 against the valve flap 69. The adjustable screw 82 can be turned to increase or decrease the compressive force of the spring 40 on the valve flap 69 against additive port 76 thereby increasing or decreasing the primary flow force required to deflect the tongue 70 and gate means 43 to open the additive flow port 76. It is envisioned that the adjustment means 81 may be eliminated, once emperical testing indicates the proper strength for spring 40.

Manual control means 90 are provided to overcome the force of the spring 40 on the valve flap 69. The manual control means 90 is pushed by an operator to push the valve flap 69 away from the additive port 76. As shown in FIG. 7 the manual control means 90 comprises a shaft 92 which projects through a control bore 94 and has a button top 96 which is pressed upon to move the shaft 92. An "O" ring 98, which is used to seal the manual control means 90 against leaking, is secured in sealing bore 100 by annular "O" ring retaining features 101 on the shaft 92. The manual control means 90 can be locked into an open additive flow position by depressing the shaft 92 to the extent that the shaft locking ring 102 is seated in the locking ring receptacle or groove 104. Pushing the manual control means 90 forces the valve flap 69 against the spring 40 to compress the spring 40 thereby opening the additive port 76 thereby permitting the flow of the additive into the primary flow 18 to be controlled by the operator. The structure thus provided an "over ride" feature, whereby the automatic metering may be disengaged in lieu of manual operation.

When the valve flap 69 is deflected, whether by material flowing in the primary flow path 18 deflecting the tongue 70 or by manual control means 90, the flow of the additive material is indicated by the additive flow indicator means 105. The additive flow indicator means 105 comprises a flap fixturing feature 106 in which is formed a movable flap 108. The fixturing feature 106 is an integrally molded portion of the additive regulating means 42 and seats in a flap seating fixture 110 of the regulator seat feature 46 when the two body sections 36, 38 are assembled. Mounting of the fixturing feature 106 into the seating feature 110 is accomplished by inserting the male structure of the fixturing feature 106 into the female structure of the seating feature 110 and then mounting the male structure of an outlet port 114 of the downstream body section 36 into the female structure of the fixturing feature 106. The flap seating fixture 110 thus overlies the exit port of the branch of the additive flow path 31 in the body 12 such that additive material passing into the chamber 119 defined by the junction of branch 31 and the additive port 76 will produce movement of the flap 108.

Movement of the flap 108 is visible through the transparent wall material of the body sections, 36, 38. While it is preferred to construct the entire body of transparent material, it is only necessary that at least an indicator viewing window in the side of the upstream body section 36 be transparent. The flap 108 is constructed in the fixturing feature 106 by making a U-shaped cut in the face of the fixturing feature 108 thereby creating a living hinge 116 at the top of the flap 108. Thus constructed and secured the flap 108 is free to move under the influence of additive flow, providing an indicator to a person operating the device that the additive material is flowing into the primary fluid path 18.

Additives are introduced into the primary flow path 18 through the additive flow path 31 which enters the body of the device 12 through the additive flow bore 56 and additive adapter 118. Additive flows through the bore 46 past the indicator flap 108 into the additive bore/port junction 119 up through the additive flow port 76. The additive flow port 76 is shaped around the manual control shaft 92 to allow flow of additive material around this structure. When the valve flap 69 is deflected away from the additive flow port 76 the additive material flows from the port 76 into the additive flow channel or junction channel or path 80 where it mixes with the primary flow path 18.

In use, scavenged blood and other matter enters the body of the device 12 through the input adapter 48 following the primary flow path 18. Between the entry bore 50 and the exit bore 52 the flow contacts the tongue 70 which extends into the primary flow path 18. When the force of the flow on the tongue 70 is greater than a specified threshold pressure, the tongue 70 resiliently deflects towards the downstream wall 78 of the additive introduction channel 80. Deflection of the tongue 70 causes the attached valve flap 69, which covers the additive flow port 76, to deflect away from the additive flow port 76. Deflection of the tongue 70 and valve flap 69 is limited by the tear drop shaped aerodynamic projection 77, which is attached to the downstream surface of the distal end of the tongue 70, contacting the downstream wall 78 of the additive introduction channel 80.

Deflection of the valve flap 69 permits flow of the additive through the additive flow bore 56 thereby deflecting the additive flow indicator flap 108. The deflected flow indicator flap 108 indicates flow as seen through the transparent side of the body 12. The additive material next flows into the bore/port junction 112 and through the additive flow channel 76 into the additive merging channel 80 where the additive is mixed with the material in the primary flow path 18. Once the force of the flow on the tongue 70 drops below the specified threshold pressure, the tongue 70 and attached valve flap 69 begins to resiliently deflect back towards the additive introduction port 76. When the force against the tongue drops below that necessary to maintain additive flow the valve flap 69 seals against the additive introduction port 76 stopping the flow of additive material into the primary flow path 18. In a like manner to that described above, the manual control means 90 may be used to intermittently open or lock open the valve flap 69 to release additive into the primary flow path 18.

Turning now to alternative forms of the flow regulating means, FIGS. 8 and 10 illustrate two plunger type alternative embodiments of the present invention. In this regard, components and structural features similar to those discussed with respect to the embodiment of FIGS. 1 and 2 have been given simliar reference characters, and will be discussed only briefly, as their structure and function is clear.

FIG. 8 illustrates a plunger type embodiment of the flow regulating means 12 where a plunger 120 is positioned in the primary flow path 18 to restrict primary flow and control additive flow and FIG. 9 illustrates the same embodiment with the plunger 120 biased to the left as viewed by fluid flow to permit additive flow by uncovering the additive path exit port 76.

The plunger means 120 is an analogous control means to the valve flap 69 in FIG. 7 in that both control devices are moved by the flow of material through the primary flow path 18, as a function of the volume, flow rate and viscosity of the primary material, to introduce additive material into the primary flow path 18. The plunger means 120 is a rigid body whereas the valve flap 69 and the tongue 70 are resiliently deflectable. Further, the plunger means 120 has an outlet passage 114 formed through the plunger structure 10 and it is this passage 114 which is aligned with the additive introduction port 76 to allow the additive material to flow into the primary flow path 18. When the passage 114 is not aligned, FIG. 8, additive flow from port 76 is blocked.

In the use of this alternative embodiment, scavenged blood and other matter flows through the primary flow path 18 and impinges on a sloped surface 122 of the plunger means 120. When the force of the flow is sufficient to overcome the resistive force of the plunger return spring 40 the plunger 120 is moved to the left as viewed in a plunger slide feature 124. Movement of the plunger 120 within the plunger slide feature 124 is restricted by corresponding limiting lips 126 formed around the inside diameter of the plunger slide feature 124 and plunger 120. The plunger return means spring 40 is maintained in the plunger slide feature 124 between the plunger means 120 and a spring retaining block 128. Once the plunger means 120 has been sufficiently moved to at least partially align the additive outlet port 114 and the additive flow port 76 (see FIG. 9), the additive flow material flows through the plunger return spring 40 into the merging channel 80 and mixes with the material flowing in the primary flow path 18. Thus, it can be appreciated that since movement of plunger 120 is a function of fluid flow in the primary path 18, the amount of additive passing from port 76 is also a function of or controlled by fluid flow in the primary path 18.

FIG. 10 illustrates an embodiment similar to that as shown in FIGS. 3 and 4, however, the FIG. 5 embodiment permits introduction of the additive "upstream" of the plunger 120 and does not require an outlet port 114 to be formed through the plunger means 120. The operation of the embodiment of the device in FIG. 10 is generally similar to the device in FIG. 8 and 9 as described above. Additionally, the plunger 120 in FIG. 10 is also limited by a limiting protuberance 130. The protuberance 130 in conjunction with the set screw 132 adjustably limits the range of motion of the plunger 120. The embodiment in FIG. 5 permits the device 12 to be constructed of a single block of material such as plastic which is bored to create the necessary channels within the block.

An alternative embodiment of the manual control means 90, as shown in FIG. 1 and FIG. 2, has been provided for the present invention. The alternative embodiment of the manual control means 134 is illustrated in FIG. 7. This alternative embodiment of the manual control means 134 is applicable to all of the embodiments of the additive regulating devices specified in this application.

The manual control means 134 illustrated in FIG. 2 differs from the manual control means 90 in FIG. 1 in that the control means 134 shown in FIG. 7 are controlled using a spring 136 returned lockable trigger ("trigger") 138. The trigger 138 pivots about a pivot point 140 on a lever arm 142. The pivot point 140 is attached to the outside of the body of the device 12 and the lever arm 142 attaches to the trigger 138.

A living hinge 144 flexibly attaches the trigger 138 to a shaft 146 which projects through the bore 94. On the inside of the bore 94 through which the shaft 146 projects is a shaft sealing "O" ring 98 and on the outside of the bore 94 is locking means 104 which is attached to the body of the device 12. The locking means 104 flexs to accept and hold the locking ring 102 on the shaft when the trigger 138 is depressed with force sufficient to overcome the flexible retaining forces of the locking means 104. The shaft 146 projects through a cap 148 which is attached to the shaft 146 in the area between the locking ring 102 and the living hinge 144. A return spring 136 is retained on one end by the cap 148 and the locking means 104 at the other end.

In use, the trigger 138 is manually depressed to intermittently or lockably control the flow of additive material. Force applied to the trigger 138 pivots the lever arm 142 about pivot point 140. The force is transferred to move the shaft 146 through the bore 94. Eventually, with sufficient force applied to the trigger 138, the distal end 148 of the shaft 138 impinges the plunger means 120 or the flow flap 69 (depending on the embodiment employed) to move such regulating structures 120, 69 thus allowing flow of the additive material. When the force is relieved the shaft 146, which is urged away from the regulator means 120, 69 by the spring 136, ceases to impinge on the regulator structure 120, 69 and stops the flow of the additive material.

While preferred embodiments of the present invention are shown and described it is invisioned that those skilled in the art may devise various modifications without departing from the spirit and scope of the invention as defined by the claims appended hereto.

The invention is claimed as follows:

1. A flow regulating device for introducing an additive into the flow of a liquid material, said device comprising: a body divided into at least a first body section and a second body section; a primary flow path formed in said body through which liquid is designed to flow; an additive flow path formed through said body, said additive flow path being at least partially nonconcurrent with said primary flow path but having an exit port opening into said primary flow path at a selected location; additive regulating means positioned and retained between said first and second body portions proximate said selected location for regulating the flow of an additive into said primary flow path, said additive regulating means comprising an integrally formed elastomeric member having a valve portion overlying said exit port of said additive flow path, a tongue portion connected to and extending from said valve portion, such that displacement of said tongue portion will correspondingly produce unseating of said valve portion to permit additive to flow from said exit port of said additive flow path into said primary flow path.

2. A device according to claim 1 wherein said tongue portion extends into said primary flow path such that fluid material flowing therein will impinge upon said tongue portion, the degree of unseating movement of said valve portion affixed to said tongue portion is a function of said fluid material flowing in said primary flow path.

3. A device according to claim 2, further including biasing means for biasing said valve portion in a first direction wherein said valve portion blocks said flow of additive from said additive flow path, and manually operable means for unseating said valve portion to permit said flow of additive from said additive flow path.

4. A device according to claim 1, further including biasing means for biasing said valve portion in a first direction wherein said valve portion blocks said flow of additive from said additive flow path, and manually operable means for unseating said valve portion to permit said flow of additive from said additive flow path.

5. A device according to claim 3, further including flow resistance means for adjustably controlling the force created by said biasing means on said valve means thereby adjustably controlling the force required to unseat said valve portion from said exit port, said flow resistance means comprising; an adjustment screw extending through a threaded bore in said body, a disk formed on an end of said adjustment screw which is placed inside of said body, said disk movably positioned inside of said body for compressing said biasing means between said disk and a facing surface of said valve portion whereby turning said adjustment screw to compress said biasing means increases the force required to unseat said valve from said exit port.

6. A device according to claim 4, further including flow resistance means for adjustably controlling the force created by said biasing means on said valve means thereby adjustably controlling the force required to unseat said valve portion from said exit port, said flow resistance means comprising; an adjustment screw extending through a threaded bore in said body, a disk formed on an end of said adjustment screw which is placed inside of said body, said disk movably positioned inside of said body for compressing said biasing means between said disk and a facing surface of said valve portion whereby turning said adjustment screw to compress said biasing means increases the force required to unseat said valve from said exit port.

7. A device according to claim 3, wherein said tongue portion is integrally formed with an aerodynamically shaped projection on the top portion of the downstream racing surface of said tongue for reducing turbulence created by said tongue while at least partially obstructing said primary flow path and for limiting the degree of movement of said tongue.

8. A device according to claim 3, wherein said manually operable additive control means further comprises; a displacement member bore formed through said body for receiving a displacement member therethrough capable of contacting said additive regulating means, a displacement member passing through said displacement member bore for transferring a force created external to said body to displace said additive regulating means within said body, and a manual control trigger being operatively coupled with said displacement members for moving said displacement member from the outside of said body for manually controlling said additive flow.

9. A flow regulating device for introducing an additive into the flow of a liquid material, said device comprising: a body divided into at least a first body section and a second body section, one section of said body having a transparent portion; a primary flow path formed in said body through which liquid flows; an additive flow path formed through said body, said additive flow path at least partially nonconcurrent with said primary flow path and having an additive bore and an additive port connected to said primary flow path, a first port between said additive bore and said additive port is overlied by an additive flow indicator means having a flap which is displaced when additive flows through said additive bore, said additive flow indicator means provides a visual indication of additive flowing through said additive bore; said transparent portion of said body located coincident with said first port permitting observation of said additive flow indicator through said body; additive regulating means operationally positioned in said body proximate said selected location for regulating the flow of additive into said primary flow path, said additive regulating means comprising an integrally formed elastomeric member including said valve portion overlying said exit port of said additive flow path, said additive flow indicator means and a tongue portion connected to and extending from said valve portion, displacement of said tongue portion producing unseating of said valve portion for permitting additive to flow from said exit port of said additive flow path into said primary flow path.

10. A flow regulating device for introducing an additive into the flow of a liquid material, said device comprising: a body having at least two body sections with a seam which generally perpendicularly intersects a primary flow path formed therethrough; an additive flow path formed through said body, said additive flow path being at least partially nonconcurrent with said primary flow path and having an exit port opening into said primary flow path at a selected location; additive regulating means positioned and retained between said at least two body sections proximate said selected location for regulating the flow on an additive into said primary flow path, said additive regulating means comprising an integrally formed elastomeric member having an annular gasket means for sealing said at least two body sections to prevent leakage when said body sections are joined, a valve portion overlying said exit port of said additive flow path and a tongue portion connected to and extending from said valve portion, such that displacement of said tongue portion will correspondingly produce unseating of said valve portion to permit additive to flow from said exit port of said additive flow path into said primary flow path.

* * * * *